(12) United States Patent
Ferkovich et al.

(10) Patent No.: US 7,354,611 B1
(45) Date of Patent: Apr. 8, 2008

(54) FECUNDITY-PROMOTING SUPPLEMENT FOR THE INSIDIOUS FLOWER BUG REARED ON ARTIFICIAL DIET

(75) Inventors: Stephen M. Ferkovich, Gainesville, FL (US); Jeffrey Shapiro, Gainesville, FL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 573 days.

(21) Appl. No.: 10/721,881

(22) Filed: Nov. 26, 2003

(51) Int. Cl.
*A01K 97/04* (2006.01)

(52) U.S. Cl. .............................. 426/1; 426/2; 435/348; 119/6.6

(58) Field of Classification Search .................... 426/1, 426/2; 435/348; 119/6.6
See application file for complete search history.

(56) References Cited

U.S. PATENT DOCUMENTS

| 5,834,177 | A | 11/1998 | Cohen |
| 5,945,271 | A | 8/1999 | Cohen |
| 6,129,935 | A | 10/2000 | White et al. |
| 6,291,007 | B1 | 9/2001 | White et al. |

OTHER PUBLICATIONS

AgAttack. Artificial Diet for Orius. Author: Orr. Published Apr. 9, 2000. <http://www.agattack.com/students.htm>.*

\* cited by examiner

*Primary Examiner*—Anthony Weier
(74) *Attorney, Agent, or Firm*—John Fado; Gail Poulos (57) ABSTRACT

A new protein supplement for insect rearing contains extracts of insect eggs or cultured insect egg embryonic cell lines from insects such as *Plodia interpunctella* and *Ephestia kuehniella* Zeller, etc., to increase the fecundity of insects reared for biocontrol.

6 Claims, 6 Drawing Sheets

FECUNDITY-PROMOTING SUPPLEMENT FOR THE INSIDIOUS FLOWER BUG REARED ON ARTIFICIAL DIET

BACKGROUND OF THE INVENTION

1. Field of the Invention

The present invention relates to insect artificial media protein supplement derived from eggs of insects used for rearing beneficial insects such as, for example, the Indian meal moth, *Plodia interpunctella*, the Mediterranean flour moth, *Ephestia kuehniella*, etc., which can enhance the fecundity of beneficial insects such as, for example, the insidious flower bug, *Orius insidiosus*, reared on an artificial diet. It also relates to the use of the supplements in an artificial insect diet as well as an artificial diet containing at least one of the protein supplements.

2. Description of the Related Art

One of the greatest needs in the field of biological control is to be able to produce insect natural enemies such as predaceous and parasitic beneficial insects at a reasonable cost so that they can be used in lieu of conventional pest control. In the United States and throughout the world, the application of synthetic chemical insecticides is the primary method of controlling insect pests of many agricultural commodities, including food, fiber, and ornamental crops. However, there is an increasing interest in reducing the use of chemical pesticides and fertilizers and to make agriculture more sustainable. Biological control is recognized as the best alternative to the use of chemical insecticides for controlling insect pests.

A major stumbling block to using biological control on a large scale as an alternative to pesticides is that it has been impossible to produce adequate numbers of predatory insects to effect reduction of large outbreaks of pest populations. For example, arthropod predators and parasites have been used successfully for decades to control insect pests, however, the scale of their use has been limited because of inadequate methods of economically producing these predatory insects. Thus, one of the greatest needs in the field of biological control of insects is the mass production of insects's natural enemies at a reasonable cost. However, despite intensive research, for many years, on artificial media suitable for rearing predatory insects, it is still necessary to rear these beneficial insects on their natural hosts/prey or on unnatural factitious hosts. These classical methods are too expensive to allow large scale use of beneficial insects in commercial agriculture. (Grenier et al, IN: Pest Management in the Subtropic, Rosen et al. Eds., 181-201, Intercept, Andover, 1994).

The scientific literature has reported that the feeding behavior of predatory insects involves feeding on hemolymph and/or body fluids from impaled prey. For example, the larva of nearly all neuropterans, which include some of the most important families in biological control, such as for example, Chrysopidae (Green lacewings) and Hemerobiidae (brown lacewings), which attack many agricultural pests including whiteflies, aphids, scale insects, and mealy bugs, possess long curved mandibles which act like forceps to grasp and pierce the prey and suck out the body fluids (Debach, Biological Control by Natural Enemies, Cambridge University Press, 1974). Further, Debach shows the predatory big-eyed bug Geocoris, another predatory insect useful for biocontrol of important economic crop insects, sucking body fluids of its prey through its proboscis. Thus, the predator feeding models in the literature suggested that the best artificial medium for these liquid feeders should have a liquid form. E. S. Vanderzant (Journal of Economic Entomology, Volume 63, 336-338, 1973) and S. A. Hassan and K. S. Hagen (Zeitschrift fur angewante Entomologie, Volume 86, 315-320, 1978) report liquid diets for rearing *Chrysopa carnea* Stephens (lacewings) larvae. More recently, semi-solid meat-based artificial diets have been described for rearing *Geocoris punctipes* (Say) (A. C. Cohen, and N. M. Urias, The Southwestern Entomologist, Volume 11, 171-176, 1986); A. C. Cohen and R. T. Staten in Applications of Genetics to Arthropods of Biological Control Significance, Eds. S. K. Narang et al., CRC Press, Inc., Chapter 7, 121-132, 1994).

Grenier et al. (supra) present a review of over a half century of research on development of artificial media for ectoparasitoids and predators. However, in spite of the importance of predatory insects as biological control agents for economically important insect pests, very few of these artificial media are in use in the commercial production of any entomophage. Thus, production of these beneficial insects still involves the costly method of rearing them on their natural hosts/prey or on unnatural factitious hosts.

The insidious flower bug, *Orius insidiosus* (Say) (Hemiptera: Anthocoridae) is a polyphagous predator of thrips, spider mites, aphids, and insect eggs and small larvae. This predator can be reared on an artificial diet devoid of insect components; however, the females have poor fecundity. *Orius insidiosus* is produced on natural hosts by more than 33 commercial producers of beneficials (Assoc. Natur. Biocontrol Producers, 2001). Although *Orius* spp. feed on plant material such as pollen and beans, fecundity is highest in prey-reared females (Kiman and Yeargan, Ann. Entom. Soc. Am., Volume 78, 464-467, 1985; Richards and Schmidt, Entomol. Exp. Appl., Volume 80, 325-333 1996; Vacante et al., Entomophagia, Vomume 42, 493-498 1997). Thus, insectaries generally rear *Orius* species on eggs of the Mediterranean flour moth, *Ephestia kuehniella* Zeller, which are expensive, and a cheaper alternative is needed for commercial rearing. Although rearing methods for producing *O. insidiosus* on natural prey are published (Castane and Zalom, Biol. Control, Volume 4, 88-91 1994; Schmit et al., Canadian Entomol., Volume 127, 445-447 1995), an economical artificial diet that would produce *O. insidiosus* with high fecundity is needed to streamline and reduce the cost of production (Waage et al., In: R. Singh and R. F. Morre (Eds.), Handbook of Insect Rearing, Elsevier, New York, 45-66 1985; Yazlovetsky, In: T. E. Anderson and N. C. Leppla (Eds), Advances in Insect Rearing for Research and Pest Management, Westview Press Inc., Boulder, Colo., 41-62 1992; Vinson, 1994; Thompson and Hagen, In: T. S. Bellows and T. W. Fisher (Eds), Handbook of Biological Control, Academic Press, New York, 594-652, 1999). Currently the types of nutrients that affect *O. insidiosus* in an artificial diet are unknown.

Weiru and Ren (Chinese Jour. Biol. Control, Volume 5, 9-12, 1989) reared *Orius sauteri* on artificial diet composed of chicken egg yolk, soy protein, and brewer's yeast, but they did not report the fecundity of females produced.

There remains a need in the art for an effective diet for rearing beneficial insects such as, for example, *Orius* species that improves the fecundity of females. The present invention provides protein supplements which will significantly improve fecundity when added to an artificial diet. These protein supplements are different from prior art artificial diets for rearing beneficial insects such as *Orius* spp.

SUMMARY OF THE INVENTION

It is, therefore, an object of the present invention to provide protein extracts from eggs from host insects as supplements for artificial diets for beneficial insects to increase their fecundity.

A further object of the present invention is to provide an artificial diet for beneficial insect rearing that includes protein extracts of eggs from host insects such as, for example, *Plodia interpunctella*, *Ephestia kuehniella* Zeller, etc.

A still further object of the present invention is to provide an artificial diet for rearing beneficial insects that includes protein extracts of eggs from host insects in amounts effective to increase the fecundity of the reared beneficial insect.

Another object of the present invention is to provide a method for rearing beneficial insects with increased fecundity on an artificial diet having a protein extract of eggs from host insects.

A still further object of the present invention is to provide a method for rearing beneficial insects with increased fecundity on an artificial diet having protein extracts of eggs from host insects in amounts effective to increase fecundity of the reared beneficial insect.

A further object of the present invention is to provide an artificial diet for beneficial insect rearing that includes a supplement of protein extracts of eggs from host insects such as, for example, *Plodia interpunctella*, *Ephestia kuehniella* Zeller, etc., that has been further purified by isoelectric focusing and anion exchange column chromatography.

A still further object of the present invention is to provide an artificial diet for rearing beneficial insects that includes a supplement of protein extracts of eggs from host insects further purified by isoelectric focusing and anion exchange chromatography in amounts effective to increase the fecundity of the reared beneficial insect.

Another object of the present invention is to provide a method for rearing beneficial insects with increased fecundity on an artificial diet that contains a protein extract of eggs from host insects, further purified by isoelectric focusing and anion exchange chromatography.

A still further object of the present invention is to provide a method for rearing beneficial insects on an artificial diet that contains a protein extract of eggs from host insects, further purified by isoelectric focusing and anion exchange chromatography in amounts effective to increase the fecundity of the reared beneficial insect.

Another object of the present invention is to provide an artificial diet for rearing beneficial insects that includes g pelletized cells from insect cell lines derived from insect hosts in amounts effective to increase fecundity of the reared beneficial insects.

A still further object of the present invention is to provide a method for rearing beneficial insects with increased fecundity on an artificial diet that includes pelletized cells from insect cell lines derived from insect hosts in amounts effective to increase fecundity of the reared beneficial insect.

Another object of the present invention is to provide an artificial diet for rearing beneficial insects that includes homogenized pelletized cells from a beneficial insect host embryonic egg cell line in amounts effective to increase fecundity of the reared beneficial insects.

Another object of the present invention is to provide an artificial diet for rearing beneficial insects that includes a protein extract from isoelectric focusing of homogenized pelletized cells from a beneficial insect host embryonic egg cell line in amounts effective to increase fecundity of the reared beneficial insects.

Another object of the present invention is to provide a method for rearing beneficial insects with increased fecundity on an artificial diet having a protein extract from isoelectric focusing of homogenized, pelletized cells from beneficial insect host embryonic egg cell line in amounts effective to increase fecundity of the reared beneficial insect.

A still further object of the present invention is to provide a method for rearing beneficial insects with increased fecundity on an artificial diet having a protein extract from isoelectric focusing of homogenized pelletized cells from beneficial insect host egg cell line in amounts effective to increase fecundity of the reared beneficial insect.

Further objects and advantages of the present invention will become apparent from following description.

DETAILED DESCRIPTION OF THE INVENTION

Mass rearing of beneficial insects as biocontrol agents is important given the concerns about the use of chemical insecticides which create, for example, insecticide residues on commodities, resistance of insects to chemical insecticides, hazardous exposure to pesticide applicators, environmental contamination, and destruction of natural biocontrol agents such as beneficial insects. Furthermore, as pests become more resistant to pesticides, more frequent treatments are required which increases the human health hazard.

An alternative to chemical pesticides is the use of biocontrol agents such as beneficial insects which include predaceous and parasitic insects which kill harmful pests. The development of artificial diets and in vitro rearing procedures is important to enable the use of beneficial insects in pest management. This use could have tremendous economic and environmental impact. For example, for one commodity, cotton, the total cost for arthropod pests, including control costs plus losses, is on the order of approximately $685 million annually.

A supplement for insect culture media containing beneficial insect host insect egg protein extract or pelletized cells from a beneficial insect egg host embryonic cell line has been discovered.

The supplement of this invention is applicable to any insect, particularly beneficial insects such as predaceous and parasitic insects. Such insects include, but are not limited to, insects from the orders Hemiptera, Hymenoptera, Diptera, Heteroptera and Neuroptera. Examples include *Orius insidiosus, Geocoris punctipes, Podisus maculiventris, Perillus bioculatus, Lyctocoris campestris*, and *Xylocoris flavipes*, all hemipterans; *Calosoma sycophanta* and *Colemegilla maculata*, coelopterans; and *Diapetimorpha introita* and *Cryptus albitarsus*, hymenopterans.

Beneficial insect host eggs, for purposes of the present invention, is intended to mean the eggs of any insect that a beneficial insect uses to feed on.

The term insect egg protein extract supplement means any supplement for insect culture media which enables an adult insect to develop and have improved fecundity without the addition of other insect components.

The protein extract of host eggs means any extract of eggs from the specified host insects that has been further purified by removing molecules of less than about 1,800 daltons molecular weight. It may contain macromolecules other than proteins but greater than about 1,800 daltons molecular weight.

The term insect egg protein extract supplement means any supplement for insect culture media that enables an adult insect to develop and have improved fecundity without the addition of other insect components. The protein extract or protein supplement in the form of pelletized cells from cultured insect egg embryonic cell lines is added in amounts effective to improve fecundity over the same media without the supplement. As used herein, in amounts effective, an effective amount, refer to the amount of supplement added to a defined insect culture medium in order to rear insects to adulthood with improved fecundity. As used herein, a defined culture medium is a medium of known components. The term complete medium is a defined medium containing the supplement of the present invention.

*Orius insidiosus* reared on an artificial diet of brewers yeast, sucrose, soy protein acid hydrolysate, palmitic acid, chicken egg yolk, and honey, as reported by Weiru and Ren (1989, supra) for *Orius sauteri* showed a reduced fecundity of *O. insidiosus* when they were maintained on the diet from the day of emergence through the end of the egg-laying cycle. When the predator *Perillus biocalatus* (F.) was maintained on an artificial diet, reduced fecundity was attributed to the failure to form mature follicles (Adams, Ann. Entomol. soc. Amer., Volume 93, 1288-1293, 2000). The decreased fecundity was thought to be due to either a reduction in the juvenile hormone titer needed for vitellogenin synthesis, or to a lack of vitellogenin precursors such as amino acids, lipids, or carbohydrates. Improved development of the predator *Perillus bioculatus* (F.) was attributed to the quality of dietary protein. Tuna fish promoted development better than other protein sources such as beef, veal, and chicken. However, a reduction in fecundity with a suboptimal diet was attributed not only to a protein deficiency but also to a lack of chemical or behavior cues that confirmed the presence of live prey (Rojas et al., J. Econ. Entomol., Volume 89, 1095-1104, 2000).

The insect egg protein extract of the present invention is prepared by homogenizing eggs from insects known to be a food source for predator or predaceous beneficial insects. The eggs are collected about 24 hours after being laid and frozen at about −85° C. Eggs may be purchased frozen from a commercial source. The eggs are homogenized on ice in a Polytron homogenizer at full speed for at least about 2 minutes using any buffer useful for preparing a protein solution, such as an ammonium acetate buffer. Ammonium acetate buffer is useful since it is removed by sublimation when the protein solution is freeze-dried. One of ordinary skill in the art could readily determine what type of buffer to use. The homogenate is centrifuged at about 16,000×g to about 20,200×g for about 5 minutes, with about 20,200×g preferred. The soluble protein is located in the middle layer of the three layer supernatant. The soluble protein is collected and filtered using about a 0.45-μm filter. The filtrate is applied to a desalting column to collect the proteins eluting in the void volume of the column. About one-milliliter fractions are collected monitoring for protein levels at about 280 nm. The protein fractions are combined, frozen in a dry ice/methanol bath, and freeze-dried. The freeze-dried protein is then dissolved in sterile distilled water for use. Protein concentration is determined using any standard procedure known in the art such as the Lowery procedure. Approximately 0.3-4.0 mg/ml, preferably about 0.5 mg protein/ml of media is used to increase fecundity of reared female insects. The protein extract can be further purified by isoelectric focusing from about pH 4.0 to about pH 10, collecting about 2 ml fractions. NaCl is added to each fraction to give about a 1 M concentration and dialyzed against physiological saline to remove ampholytes. The protein fractions are then bioassayed to determine which fraction contains the active protein. This purified protein supplement is then added to the artificial media at a concentration of from about 300 μg protein/ml media to about 500 μg protein/ml media.

Protein was also purified from extracts of host eggs by anion exchange chromatography. Eggs are homogenized as above, but prior to desalting, the homogenate is injected onto a medium pressure anion exchange chromatography column (Pharmacia HR10/10 packed with Source 15Q media). Following injection of extract of host eggs, about 1 gram of extracted eggs, a gradient of about 50 mM TRIS buffer, pH about 8.5, to the same buffer with about 0.2 mM NaCl added, was run over about 5 minutes, held about 5 minutes and followed by a gradient of about 50 mM Sodium Acetate buffer, pH about 5.0, containing about 0.2 M NaCl, run over about 5 minutes. Absorbance was detected at about 280 nm and about 260 nm and peak fractions were pooled and bioassayed.

For pelletized embryonic insect egg cells, beneficial insect host egg cell lines are cultured in Grace's insect medium modified with approximately 10% fetal bovine serum and grown to densities of approximately $3.7 \times 10^6$ cells/ml in 250 ml Spinner flasks. The cells are harvested by centrifugation, and washed at least 2× with physiological saline. Pelletized cells can be added directly to the artificial media using about 35 μg protein/ml media to about 200 μg protein/ml media and homogenized in the diet using an ultrasonic cell disrupter for about 10 seconds. Or the cells can be homogenized and then added to the media at the above concentrations of protein or the homogenized preparation can be further purified as described above to obtain a purified preparation.

The following examples are intended to further illustrate the invention and are not intended to limit the scope of the invention as defined by the claims. The beneficial insect *Orius insidiosus* and the beneficial insect host eggs from *Plodia interpunctella* and *Ephestia Kuehniella* are used as a model system.

EXAMPLE 1

Newly emerged adults of *Orius insidiosus* (<24 hour eclosion) were obtained from a commercial producer of beneficial insects (Entomos, Gainesville, Fla.). The insects were placed on the experimental diets on the third day after eclosion. Each diet treatment consisted of six females and four males in a 100-ml plant tissue culture jar (Sigma, St. Louis, Mo.) with four jars per treatment. Each jar contained one paraffin-encapsulated water dome (50 µl), two artificial diet domes (50 µl), one 7-cm section of green bean pod for oviposition, and three crumpled strips of wax paper (5 mm×80 mm) as substrates for the insects to crawl on. Artificial diet jars contained only artificial diet. Experimental diet jars contained artificial diet plus a supplement. *Plodia* egg (standard) jars each contained approximately 75 *Ploida interpunctella* eggs (approximately 3 mg) in place of diet. Although eggs from *Euphestia kuehniella* are generally used by commercial producers, eggs from *P. interpunctella* were used because *O. insidiosus* feeds readily on their eggs. Green beans were removed every other day and examined under a microscope to count eggs and then replaced with a fresh green bean section and mortality was also recorded within each jar. *Plodia* eggs and domes of water and diet were replaced on the same days that the green beans were removed for counting eggs. The insects were held in a growth chamber at about 25.50±1° C., with approximately 75±5% relative humidity, and a photoperiod of 15:9 (light: dark) hours. The experiments were carried out until the females in all treatments ceased oviposition, approximately 28 days. Diets were prepared under aseptic conditions in a clean room and encapsulated in Parafilm using a diet encapsulation apparatus as described in Ferkovich et al. (BioControl, Volume 45, 401-413, 2000).

The artificial diet was developed for rearing *Orius sauteri* (Weiru and Ren, 1989, supra), and consisted of approximately 4.0 grams brewers yeast, 0.4 grams sucrose, 2.1 grams soy protein acid hydrolysate, 0.046 grams of 99% palmitic acid (all from Sigma, St. Louis, Mo.), 0.5 grams chicken egg yolk, and 1.0 gram honey in 12 ml distilled water. Palmitic acid was mixed with the egg yolk component before adding it to the diet.

The standard diet consists of *Plodia* eggs. Eggs were obtained from a laboratory colony of *Plodia interpunctella* reared on a standard diet with a controlled temperature and relative humidity as described by Silhacek and Miller (Ann. Entomol. Soc. Am., Volume 65, 1084-1087, 1972). The *Plodia* diet consisted of Gaines® dog meal (ground), rolled oats, white cornmeal, whole wheat flour, wheat germ, brewers yeast, glycerol, and honey. Eggs were collected within one hour after oviposition, held at about 4° C. for approximately 24 hours, and then stored at about −80° C. until used in the study.

The experimental diets were composed of artificial diet supplemented with either components from eggs of *P. interpunctella* or noninsect nutrients available commercially. The first supplement was *Plodia* egg homogenate. Eggs at about 0.5 gram, 0.75 gram, and 1 gram were each homogenized on ice in about 2 ml distilled water or about 20 mM Tris-HCl, pH about 7.0, in a hand-held glass homogenizer and immediately added to the diet to give concentrations of about 41.6, 62.5, and 83.3 mg/ml.

A second supplement was a *Plodia* egg extract. Approximately 5 grams of *P. interpunctella* eggs (approximately $1.25 \times 10^6$ eggs) were homogenized on ice using a Polytron™ homogenizer with about a 1 cm diameter generator (Brinkman, Westbury, N.Y.) for about 2 minutes at full speed in about 20 ml of ammonium acetate buffer (about 1.16 g/L, titrated to pH about 7.5 using ammonium hydroxide). The homogenates were centrifuged at about 20,200×g for about 5 minutes. The supernatant contained three layers following centrifugation. Soluble protein in the middle layer (beneath the upper lipid layer) was collected and filtered through a Millex-HV™ 0.45-µm/29-mm dia. filter (Millipore, Bedford, Mass.). The supernatant was applied in about 1.25 ml aliquots to a D-Salt Excellulose desalting column (Pierce, Rockford, Ill.) equilibrated in ammonium acetate buffer, eluted in about 1 ml fractions, and proteins were monitored at about 280 nm and collected in the void volume. These fractions were combined (about 37 ml), frozen in a dry ice/methanol bath, and freeze-dried, resulting in a fluffy white powder. The freeze-dried desalted powder (about 325 mg) was added to about 5 ml distilled water, the soluble protein concentration of the solution was determined to be about 17.9 mg/ml using the Lowery procedure for soluble proteins (Protein Assay Kit, Sigma, St. Louis, Mo.). Aliquots of about 0.75, 1.0, and 2.0 ml of the protein solution were each added to about 12 ml of diet to give final concentrations of approximately 0.2, 0.3, and 0.5 mg/ml of diet, respectively.

The third supplement was a *Plodia* egg lipid extract. Lipids were extracted from about 0.5 gram, 0.75 gram, and 1 gram of *Plodia* eggs using a modified method of Folch et al. (J. Biol. Chem., Volume 226, 497-509, 1957) according to Ferkovich (Biocontrol, Volume 45, 401-413, 2000; herein incorporated by reference). Briefly, a chloroform:methanol (approximately 2:1, v:v) was added to about 12 ml of egg homogenate in Ringer's solution at a ratio of about 1 ml homogenate to about 6 ml of chloroform:methanol. The emulsion was broken with distilled water (about 73.3 ml) and each of the two resultant chloroform and methanol phases were dried down to approximately 0.5 ml at about 40° C. using a Rotovap™. Any noticeable solvent residue was removed by blowing purified nitrogen into the flask. Solvent controls were prepared by extracting Ringer's solution with the chloroform:methanol mixture and drying. The egg yolk component of the diet was added to the flask containing the lipid residue and then rotated for about 5 minutes.

The fourth supplement was made up of fatty acids based on the fatty acid profile of *Plodia* eggs. About a one half gram of *Plodia* eggs were analyzed for fatty acids by gas chromatography using the MIDI Sherlock Microbial Identification System (Department of Entomology, University of Florida, Gainesville, Fla.). About a 0.5 gram quantity of *Plodia* eggs (<12 hours after oviposition) was frozen, homogenized in liquid nitrogen, extracted, separated (phenyl methyl silicone fused silica capillary column), and identified according to Sasser (1997). Based on the fatty acid analysis of *Plodia* eggs, the three predominant fatty acids, palmitic (about 34.9%), linoleic (about 18.36%), and oleic (about 36.58%), all from Sigma, were mixed in the chicken egg yolk portion of the diet and added to the diet in the appropriate concentrations of about 183.3, 350.0, and 367.0 mg/ml of diet for linoleic, palmitic, and oleic acids, respectively. This resulted in a total concentration of about 900 mg of fatty acids/ml of diet.

The non-insect supplements were chicken liver, beef liver, chicken egg albumin, and bovine serum albumin (BSA).

Ground chicken liver was added at about 125.0 and 208 mg/ml of diet and based on the average digestible protein per 100 grams of chicken liver (Souci et al., Food Composition and Nutrition Tables, Wissenschaftliche Verlagsgesellschaft mbH Stuttgart, CRC Press, Boca Raton, Fla., 1028, 1989) contained about 26.7 and 45.0 mg protein/ml of diet, respectively. Ground beef liver was added to the diet at about 125.0 and 208.3 mg/ml of diet and based on the average digestible protein per 100 g of beef liver (Souci et al., 1989, supra) contained about 25.0 and 40.8 mg protein/ml of diet, respectively. Chicken egg albumin was pasteurized chicken egg white (Deb-EL Foods, Elizabeth, N.J.) added to the diet at about 166.7 and 250.0 mg/ml of diet. Bovine Serum albumin (Fraction V powder, Sigma) was added to the diet at about 83.0 and 166.6 mg/ml of diet.

Two tests were conducted. In the first test, artificial diet was compared with the experimental diets which were composed of artificial diet supplemented with homogenized *Plodia* eggs, and protein and lipid extracts from *Plodia* eggs as described above. Each experimental diet was compared against the control artificial diet in an independent experiment on different dates. In the second test, any of the statistically significant experimental diets from the first test were then simultaneously compared with the experimental diets containing non-insect supplements.

Each treatment in both tests was replicated four times with 6 females and 4 males/replication. The cumulative number of eggs laid/female on artificial diet and on experimental diet were calculated relative to the percent eggs laid/female on *Plodia* eggs (standard); thus, mean ±S.E.= [#eggs laid per female on either artificial diet or experimental diet divided by # eggs laid per female on *Plodia* eggs]× 100, n=4. The egg counts were adjusted for mortality. The egg counts per female were calculated for each replication. Data was analyzed by ANOVA using StatMost Software (Dataxiom Software Inc.). Dunnet's test was used to determine if the cumulative number of eggs laid/female on each of the experimental diets was significantly greater than the number of eggs laid/female on artificial diet. The number of eggs laid by females on the artificial diet and experimental diets were also compared as a percentage of the number of eggs laid on the standard diet of whole *Plodia* eggs.

Figure 1:
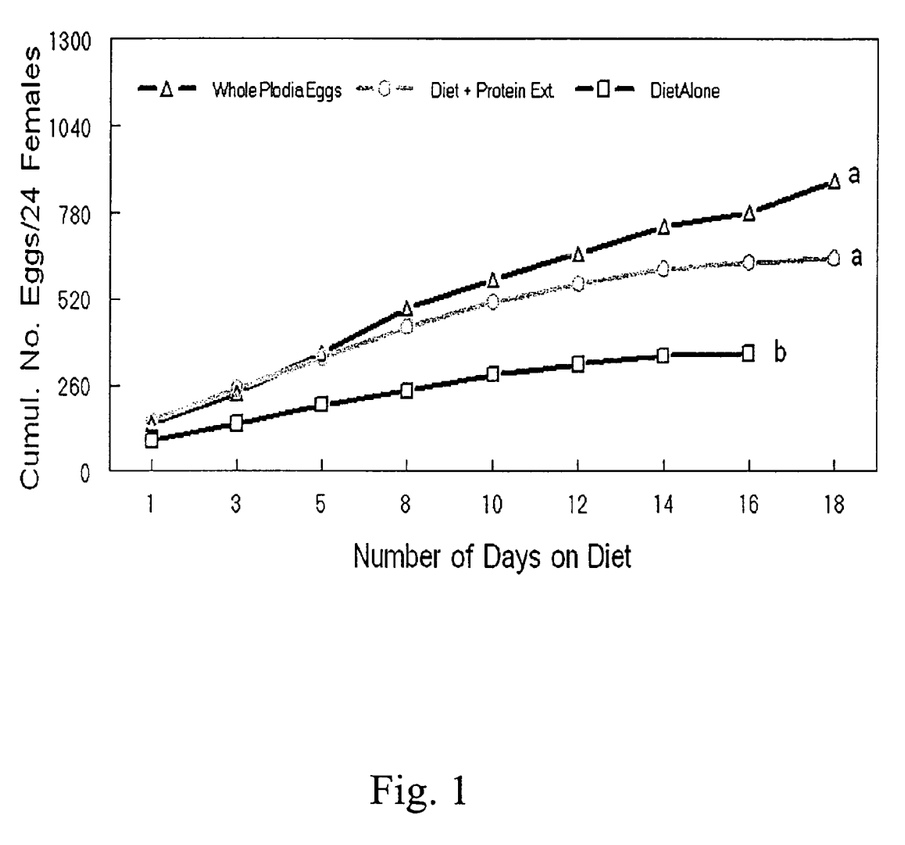
FIG. 1 is a graph showing a comparison of *Orius* cumulative oviposition rates when fed on whole *Plodia* eggs or control diet with and without *Plodia* protein extract.

In the first test, the *Plodia* egg homogenate did not increase the average cumulative number of eggs laid by females maintained on the diet (Table 1). At the highest concentration of homogenate (approximately 83.3 mg/ml), the mean number of eggs/female was significantly reduced compared to the artificial diet alone. Only females reared on diet with *Plodia* egg protein extract at approximately 0.3 mg/ml concentration laid significantly more eggs than females reared on artificial diet alone (FIG. 1). Neither the *Plodia* egg lipid extract nor the fatty acids supplement had a significant effect on the average number of eggs laid/ female.

In the second test, non-insect sources of protein were tested to see if they would increase egg production comparable to the *Plodia* egg protein extract. The *Plodia* egg protein extract and three noninsect protein sources, bovine serum albumin, chicken egg albumin, and beef liver, significantly increased the cumulative mean number of egg oviposited/female (Table 2). Egg production was significantly increased by the midlevel concentration (approximately 0.3 mg/ml) of *Plodia* egg protein extract tested relative to the artificial diet. This concentration of *Plodia* egg protein extract was approximately 80, 555, and 832× lower than the concentration needed for beef liver, bovine serum albumin, and chicken egg albumin, respectively, to significantly increase egg production.

TABLE 1

Effects of supplementing artificial diet with components from eggs of *Plodia interpunctella* and three predominant fatty acids identified in *Plodia* eggs.

| Treatment[1] | Mean no. eggs/female ± SE[2,3] | % *Plodia* egg Standard ± SE |
|---|---|---|
| *Plodia* egg homogenate (mg/ml diet) | | |
| 0 (artificial diet, control) | 10.4 ± 1.2 | 43.5 ± 0.1 |
| 41.6 | 10.0 ± 0.9 | 41.8 ± 0.0 |
| 62.5 | 8.8 ± 1.0 | 36.8 ± 0.0 |
| 83.3 | 6.6 ± 0.7* | 27.7 ± 0.0 |
| *Plodia* egg protein extract (mg/ml diet) | | |
| 0 (artificial diet, control) | 11.4 ± 0.8 | 43.9 ± 2.5 |
| 0.3 | 17.4 ± 1.3* | 65.1 ± 5.0 |
| 0.5 | 15.2 ± 1.3 | 56.8 ± 4.7 |
| *Plodia* egg lipid extract (egg equiv., mg/ml diet)[4] | | |
| 0 (artificial diet, control) | 12.8 ± 2.6 | 34.9 ± 7.0 |
| 41.6 | 12.2 ± 1.9 | 33.5 ± 4.4 |
| 62.5 | 15.4 ± 2.5 | 41.3 ± 5.7 |
| 83.3 | 15.9 ± 2.8 | 42.5 ± 7.3 |
| Fatty acids (mg/ml diet)[5] | | |
| 0 (artificial diet, control) | 12.8 ± 2.6 | 34.9 ± 7.0 |
| 900.0 | 10.5 ± 2.6 | 28.3 ± 7.1 |

[1]Each supplement was tested on a different date in an independent experiment with the artificial diet and *Plodia* eggs (standard).
[2]Mean ± SE of {#eggs laid/female on treatment/eggs laid/female on *Plodia* eggs standard × 100; n = 4, 6 female with 4 males per rep.
[3]Dunnet's test was used to compare the treatment means against the artificial diet (control); asterisk indicates that treatment means are significantly different from artificial diet (control) ($P < 0.05$).
[4]Diet supplemented with lipids extracted from approximately 0.5, 0.75, 1.0 gram of *Plodia* eggs and added to about 12 ml of diet.
[5]A mixture of linoleic (about 183.3 mg), palmitic (about 350 mg), and oleic (about 367 mg) per ml of diet.

TABLE 2

Concurrent comparison of Noninsect supplements with the *Plodia* egg protein extract that significantly improved fecundity in Test 1.

| Treatment | Mean no. eggs/female ± SE[1] | % of *Plodia* egg Standard ± SE[2] |
|---|---|---|
| Artificial diet (control) | 14.8 ± 0.5 | 38.5 ± 1.4 |
| Artificial Diet with: | | |
| *Plodia* egg protein extract (mg/ml diet) | | |
| 0.2 | 17.8 ± 1.3 | 45.1 ± 3.8 |
| 0.3 | 21.8 ± 1.9* | 56.8 ± 5.1 |
| 0.5 | 24.7 ± 0.2* | 64.2 ± 4.3 |
| Bovine Serum Albumin (mg/ml diet)[4] | | |
| 83.3 | 19.7 ± 1.6 | 51.3 ± 4.1 |
| 166.7 | 24.9 ± 1.6* | 64.9 ± 4.2 |
| Chicken Egg Albumin (mg/ml diet)[5] | | |
| 166.7 | 20.0 ± 1.0 | 52.2 ± 2.6 |
| 250.0 | 24.8 ± 0.9* | 64.6 ± 2.5 |
| Chicken Liver (mg/ml diet)[3] | | |
| 26.7 | 17.9 ± 1.4 | 46.3 ± 3.8 |
| 45.0 | 18.8 ± 1.7 | 49.0 ± 4.4 |

TABLE 2-continued

Concurrent comparison of Noninsect supplements with the *Plodia* egg protein extract that significantly improved fecundity in Test 1.

| Treatment | Mean no. eggs/female ± SE[1] | % of *Plodia* egg Standard ± SE[2] |
|---|---|---|
| Beef Liver (mg/ml diet)[3] | | |
| 25.0 | 20.9 ± 1.5* | 54.7 ± 3.8 |
| 40.8 | 15.9 ± 0.7 | 41.3 ± 1.8 |

[1]Dunnet's test was used to compare the treatment means against the artificial diet (control); asterisk indicates that treatment means are significantly different from artificial diet, (P < 0.05).
[2]Mean ± SE of {number of eggs laid/female treatment/eggs laid/female on *Plodia* eggs standard × 100}; n = 4, 6 females with 4 males per rep.
[3]The quantity of protein in the chicken and beef liver supplements added to the diet was based on average digestible protein per 100 gram as described by Souci et al. (1989 supra).

EXAMPLE 2

Figure 2:
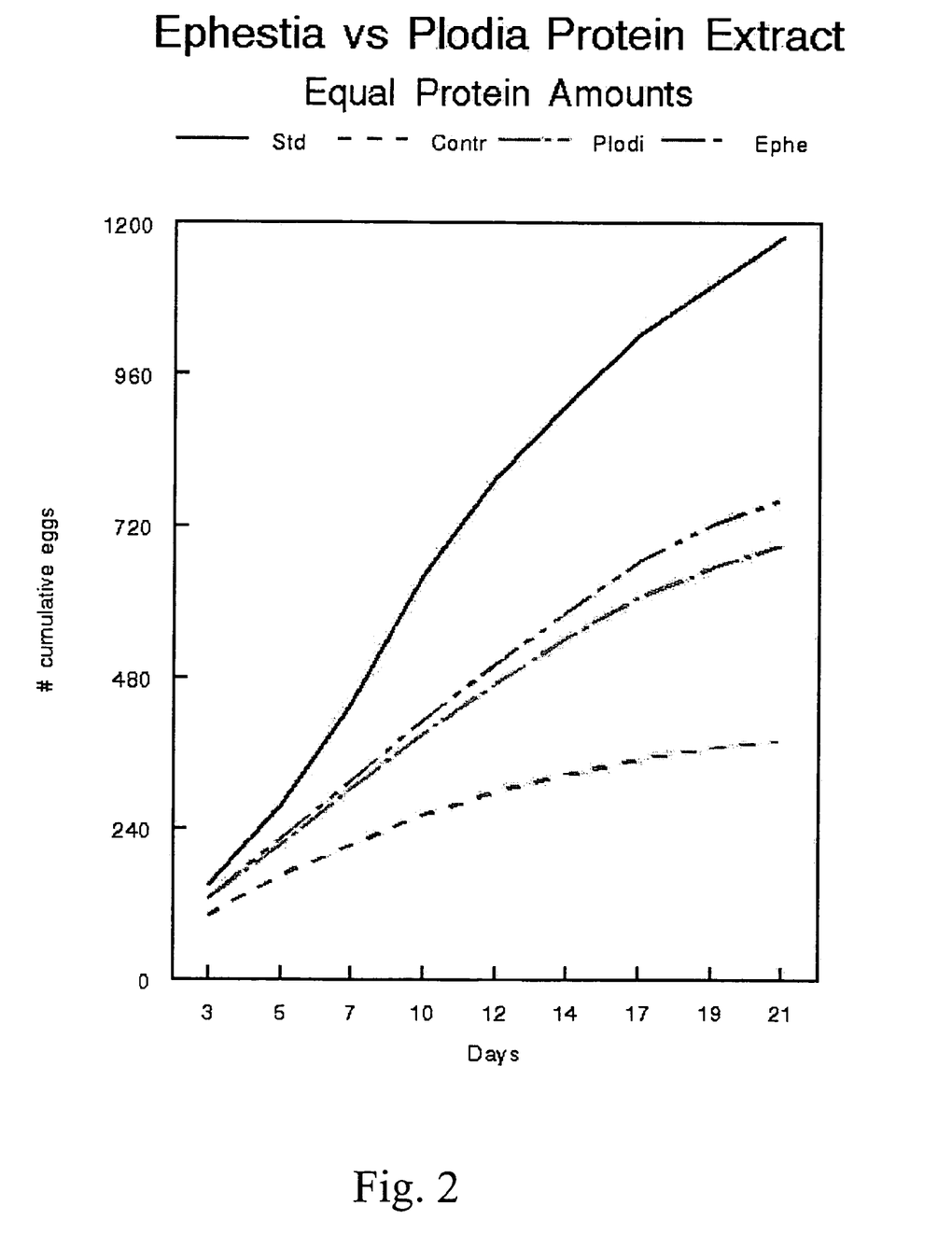
FIG. 2 is a graph showing a comparison of *Orius* cumulative oviposition rates when fed on *Plodia* eggs (Std) or control diet alone (Contr) or with added *Plodia* (Plodi) or *Ephestia* (Ephe) protein extract.
Figure 3:
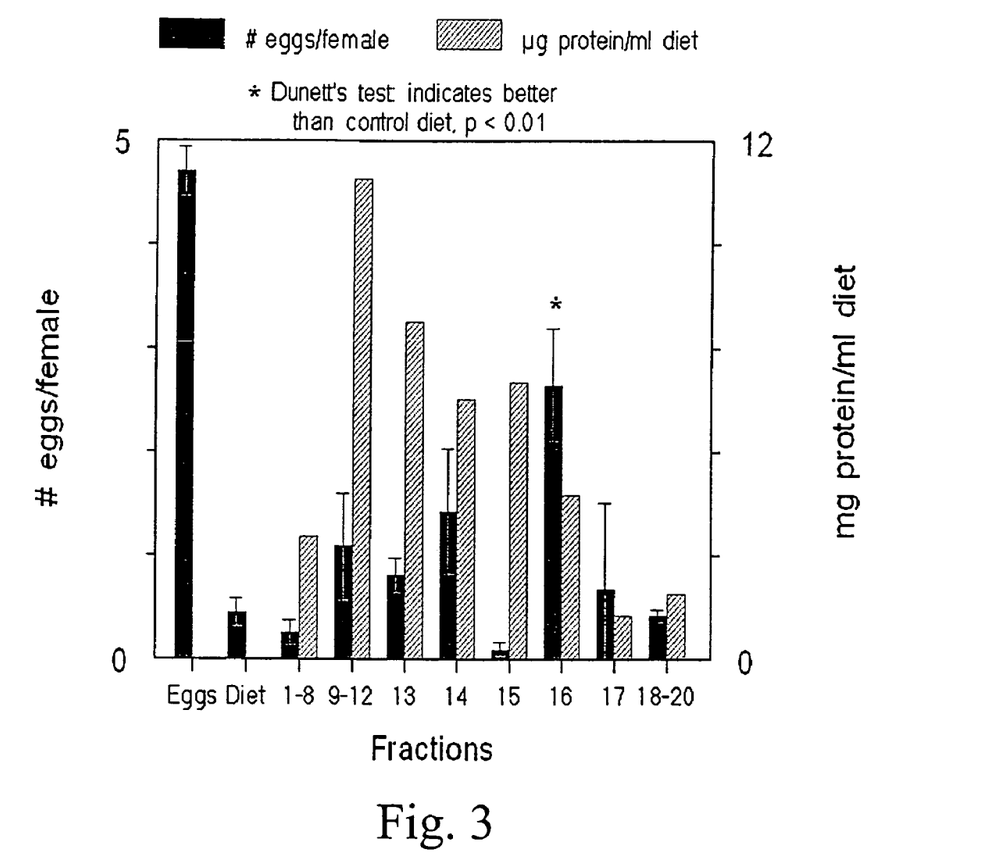
FIG. 3 is graph of a bioassay (eggs laid/female *Orius*) of isoelectric focusing fractions from *Ephestia* whole egg protein extract. Protein (µg/ml) represents the protein content of added fractions to demonstrated resulting activity despite low protein concentration.

*Ephestia kuehniella* eggs are generally used by insectaries to rear *Orius* species and egg production was about 25% higher in females fed on *Ephestia* eggs compared with those fed on *Plodia* eggs. However, FIG. 2 demonstrates that *Ephestia kuchniella* egg protein extract, prepared as described for *Plodia interpunctella* extract in Example 1, yielded egg production from *Orius* similar to those fed *Plodia* extract. The freeze-dried protein powder (approximately 480 mg) from five grams of *Ephestia* eggs was dissolved in about 33 ml of electrolyte buffer and the protein extracted was focused in an isoelectric gradient of about pH 4-10. After the voltage stabilized, the gradient of focused protein was separated into 20 fractions of approximately 2 ml each and the pH of each measured. The fractions were then brought to 1 M NaCl and then dialyzed against physiological saline to remove ampholytes. The protein concentration of each fraction was measured and the fractions were combined based on protein peaks and again analyzed for protein levels. One fraction, #16, with an isoelectric point of about pH 8.5, induced females to lay significantly more eggs than the control diet (P<0.01) (FIG. 3).

Figure 4A:
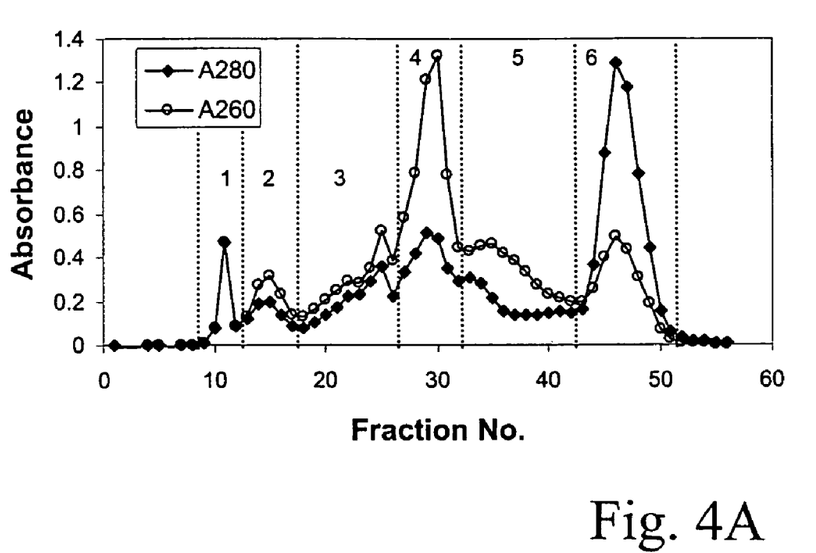
FIGS. 4a and 4b show separation of *Ephestia* egg components by anion exchange chromatography (Top-4a) and an electrophoretic gel (Bottom-4b) showing the protein components of each pooled set of fractions, with oviposition-stimulating activity and protein content below. NS=not significant.
Figure 4B:
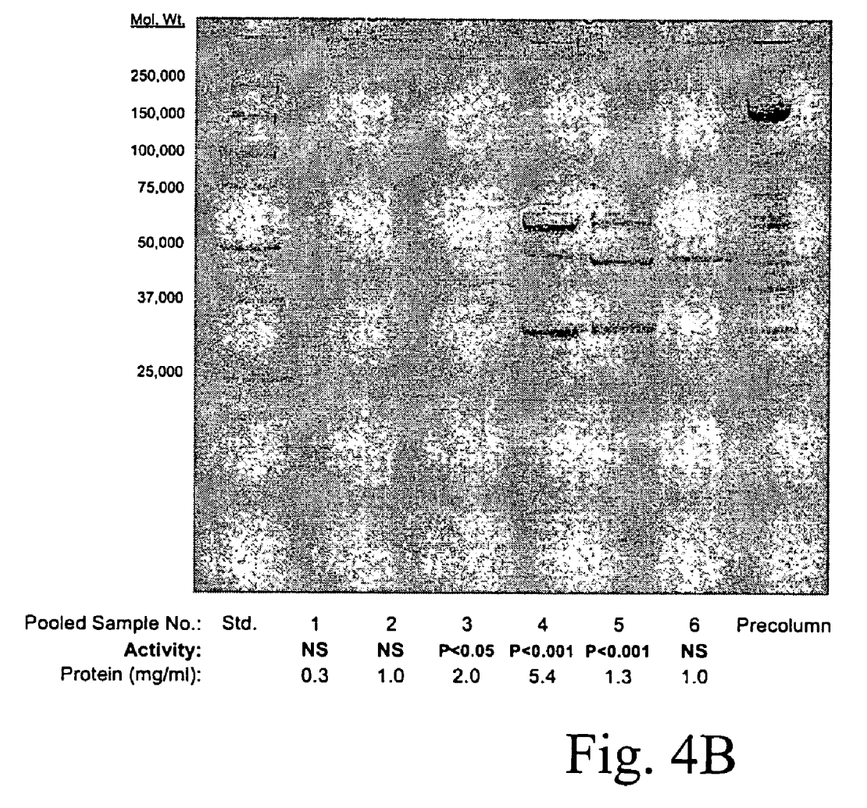

Anion exchange chromatography was also used to separate proteins in *Ephestia* egg extract. Eggs (about 1 gram) were extracted in 50 mM Tris-HCl buffer, pH of about 8.5 and applied to an anion exchange column and eluted using about 50 mM Tris-HCl plus about 0.2 M NaCL, pH about 8.5 and about 50 mM sodium acetate, pH about 5.0. Fractions from the column were pooled by chromatographic peak and tested for activity in the bioassay. Three of the six peaks, peaks 3-5, contained significant activity in the egg-laying assay. Two of these peaks, peaks 4 and 5, showed highly significant (P<0.001) activity. Three polypeptides (protein subunits) were identified by SDS gel electrophoresis (FIG. 4) as predominant in peaks 4 and 5, with molecular weights of about 35,000, 48,000 and 58,000 kDa (FIG. 4b). These peaks also showed high absorbance at about 260 nm, relative to absorbance at about 280 nm (FIG. 4a). Since such relatively high $A_{260}$ nm/$A_{280}$ nm ratios may indicate the presence of nucleic acids, nucleic acids may also contribute to activity of these fractions. Nucleic acids were also indicated by high levels of fluorescence when a DNA/RNA binding dye was mixed with these fraction; the dye fluoresced strongly, indicating the presence of nucleic acids. Alternatively, the high $A_{260}$ nm/$A_{280}$ nm ratios may indicate that the proteins noted above contain unusually low levels of aromatic amino acids, since such amino acids are responsible for high absorbance at 280 nm in polypeptides.

EXAMPLE 3

Whole cells derived from embryos of *Plodia interpunctella* were homogenized and added to control diet. Adding *Plodia* cell homogenate directly to the artificial diet at concentrations of approximately 35, 75, and 142 µg protein/ml diet showed an increase in cumulative number of eggs per female when compared to the control artificial diet. An embryonic cell line derived from the *Plodia interpunctella* embryos were grown at intermediate levels in spinner flasks. To determine whether the *Plodia* insect cell line may contain activity, cells were separated from culture medium by centrifugation and washed 2× with physiological saline, homogenized and then directly applied to the same isoelectric focusing gradient used for the *Ephestia* egg protein extract. Approximately 1.0 ml of each of the final fractions was added to the basal artificial diet. The number of eggs laid by females reared on the control diet and experimental diets were also compared as a percentage of the number of eggs laid by females reared on the standard diet of whole *Ephestia* eggs. Data were analyzed by ANOVA (Statmost software). Dunnet's test was used to determine if the cumulative number of eggs laid/female on each of the experimental diets was significantly greater than the number of eggs laid/female on the artificial control diet.

One fraction (#16) with an isoelectric point of about pH 5 induced females to lay significantly more eggs than the control diet (p<0.01). (FIG. 3).

Figure 5:
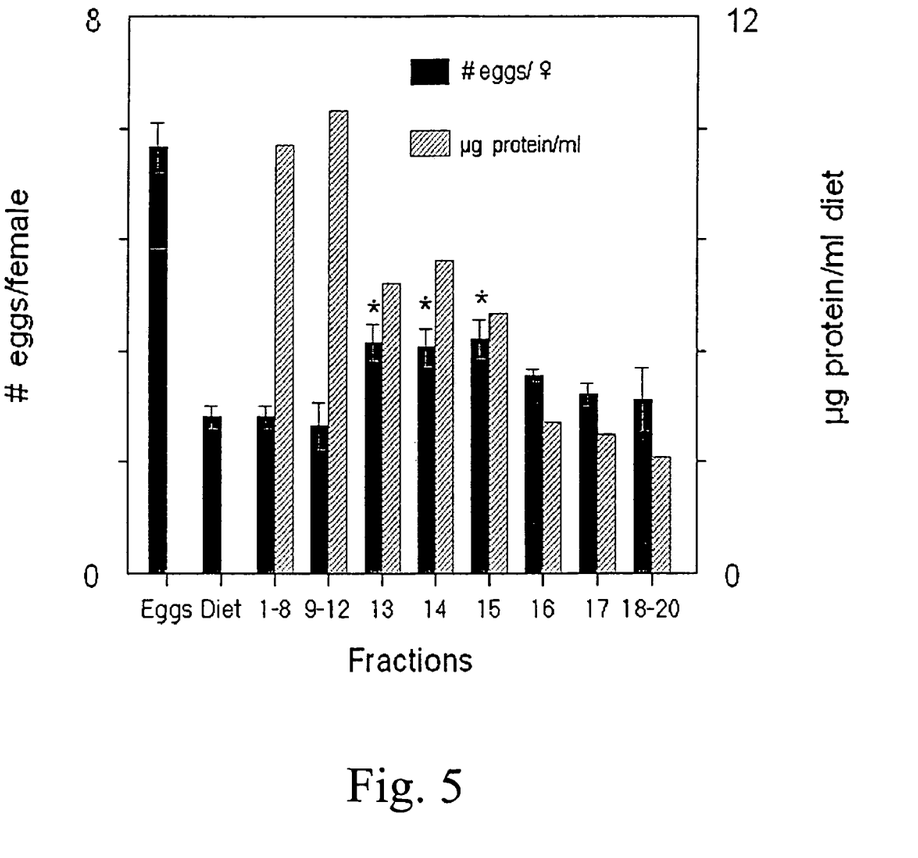
FIG. 5 is a graph showing bioassay (eggs laid/female *Orius*) of isoelectric focusing fractions from *Plodia* cell line, wherein the cultured cells are homogenized prior to isoelectric focusing. Protein (µg/ml) represents the protein content of added fraction.

Two fractions, #13 and #15, of the *Plodia* cell line with isoelectric points of about pH 7 and about pH 5.5, respectively, caused females to lay significantly more eggs (P<0.05) than the control diet (FIG. 5).

Figure 6:
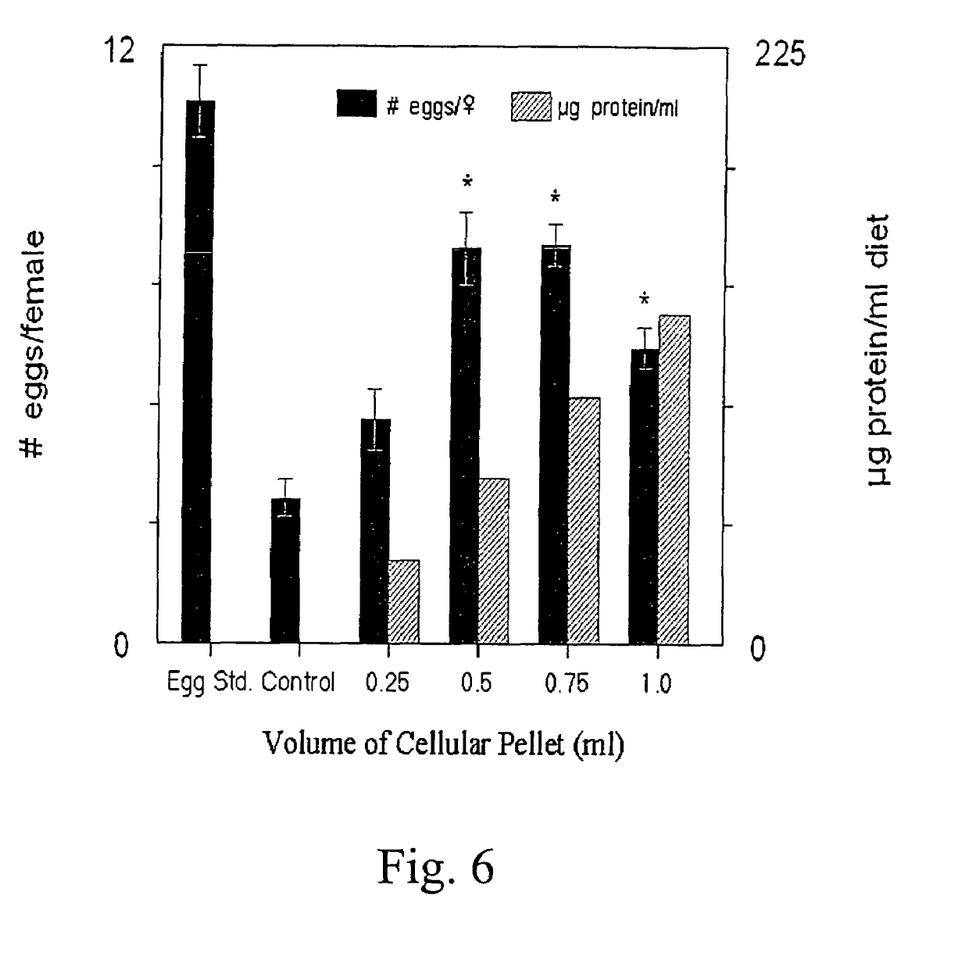
FIG. 6 is a graph showing *Orius* fecundity on artificial diet supplemented with increasing amounts of homogenized *Plodia* cellular pellet (ml). Protein (µg/ml) represents the protein content of added cells.

Furthermore, adding pelletized *Plodia* cell line pellet directly to the artificial diet at concentrations of approximately 35.0, 75.0, and 142.0 µg protein/ml diet showed an increase in cumulative number of eggs per female when compared to the control artificial diet (FIG. 6).

The foregoing detailed description is for the purpose of illustration. Such detail is solely for that purpose and those skilled in the art can make variations therein without departing from the spirit an scope of the invention.

We claim:

1. An insect egg protein supplement for rearing beneficial insects comprising:
A homogenate of host insect eggs on which a beneficial insect feeds wherein said homogenate is added in amounts effective to increase fecundity of female beneficial insects reared on an artificial diet.

2. The egg protein supplement of claim 1 wherein said egg homogenate is further purified by centrifugation, column chromatography, and isoelectric focusing.

3. The supplement of claim 1 wherein said host insect egg is selected from the group consisting of *Plodia interpunctella* and *Ephestia kneuniella* and said beneficial insect is *Orius insidiousus*.

4. An artificial medium for rearing beneficial insects comprising:
a homogenate of host insect eggs on which a beneficial insect feeds wherein said homogenate is added in amounts effective to increase fecundity of female beneficial insects on reared diet.

5. The artificial medium of claim 4 wherein said egg homogenate is further purified by centrifugation, column chromatography, and isoelectric focusing.

6. The artificial medium of claim 4 wherein said host insect egg is selected from the group consisting of *Plodia interpunctella* and *Ephestia kneuniella* and said beneficial insect is *Orius insidiousus*.

* * * * *